(12) United States Patent
Chen et al.

(10) Patent No.: US 10,660,988 B2
(45) Date of Patent: May 26, 2020

(54) ACELLULAR CORNEAS, METHODS OF PRODUCING THE SAME AND USES THEREOF

(71) Applicant: Acro Biomedical Company. Ltd., Kaohsiung (TW)

(72) Inventors: Shing-Jye Chen, Taichung (TW); Fan-Wei Tseng, Taoyuan (TW); Kai-Chi Ku, Pingtung County (TW); Dar-Jen Hsieh, Kaohsiung (TW)

(73) Assignee: ACRO BIOMEDICAL COMPANY. LTD., Kaohsiung (TW)

( * ) Notice: Subject to any disclaimer, the term of this patent is extended or adjusted under 35 U.S.C. 154(b) by 0 days.

(21) Appl. No.: 15/738,644

(22) PCT Filed: Dec. 13, 2016

(86) PCT No.: PCT/CN2016/109732
§ 371 (c)(1),
(2) Date: Dec. 21, 2017

(87) PCT Pub. No.: WO2017/118266
PCT Pub. Date: Jul. 13, 2017

(65) Prior Publication Data
US 2018/0296730 A1    Oct. 18, 2018

Related U.S. Application Data

(60) Provisional application No. 62/276,238, filed on Jan. 8, 2016.

(51) Int. Cl.
*A61L 27/36* (2006.01)
*A61L 27/38* (2006.01)
*C12N 5/079* (2010.01)

(52) U.S. Cl.
CPC ....... *A61L 27/3687* (2013.01); *A61L 27/3604* (2013.01); *A61L 27/3675* (2013.01); *A61L 27/3683* (2013.01); *A61L 27/3691* (2013.01); *A61L 27/383* (2013.01); *A61L 27/3834* (2013.01); *A61L 27/3878* (2013.01); *C12N 5/0621* (2013.01); *A61L 2430/16* (2013.01); *A61L 2430/40* (2013.01)

(58) Field of Classification Search
None
See application file for complete search history.

(56) References Cited

U.S. PATENT DOCUMENTS

| | | | | |
|---|---|---|---|---|
| 10,537,663 | B2* | 1/2020 | Jung | C12Y 301/00 |
| 2003/0072677 | A1* | 4/2003 | Kafesjian | A61L 2/0011 |
| | | | | 422/33 |
| 2011/0183404 | A1* | 7/2011 | Wee | A61K 35/44 |
| | | | | 435/268 |
| 2012/0051970 | A1* | 3/2012 | Burns | A61L 2/0082 |
| | | | | 422/33 |

FOREIGN PATENT DOCUMENTS

JP    2007105081 A  *  4/2007  ............. A61L 27/00

OTHER PUBLICATIONS

Machine translation of JP-2007105081-A downloaded from the JPO on Oct. 27, 2019 (Year: 2007).*
Lee et al. Int. J. Ophthamol. (2014) 7(40); 587-593 (Year: 2014).*
Montoya et al. Tissue Eng., Part C (2009) 15(2): 191-200 (Year: 2009).*

* cited by examiner

*Primary Examiner* — Susan M Hanley

(57) ABSTRACT

A method of producing an acellular cornea includes steps of subjecting a cornea of an animal to a decellularization process, and has not the step of treating the cornea with a protease, a chelating agent, a detergent, a glycerol, or a combination thereof. When a native cornea is processed by the method, the native structure and conformation of the native cornea are preserved while immunogenic matters are reduced to a level that the thus produced cornea may serve as a three-dimensional scaffold for host cells to grow thereon after transplantation.

6 Claims, 5 Drawing Sheets

(A)

(B)

(A)

(B)

ACELLULAR CORNEAS, METHODS OF PRODUCING THE SAME AND USES THEREOF

CROSS REFERENCES

This application is a U.S. National Stage Filing under 35 U.S.C. 371 from International Patent Application Serial No. PCT/CN2016/109732, filed Dec. 13, 2016, and published on Jul. 13, 2017, which claims the priority of U.S. Ser. No. 62/276,238, filed Jan. 8, 2016, the disclosure of which are incorporated by reference herein in their entireties.

BACKGROUND OF THE INVENTION

Field of the Invention

The present disclosure in general relates to the field of methods for producing acellular corneas suitable as grafts for transplantation, and methods for treating subjects suffering from eye conditions associated with cornea damages.

Description of Related Art

There are a large number of diseases and conditions which affect the function of the cornea, many of which are serious conditions that require remedial action that includes surgery and the transplantation of cornea tissue. Porcine corneas have been regarded as the most promising replacement of human cornea, for they have a refractive index and size comparable to human corneas. However, porcine cornea xenograft has been reported to induce severe immune response (or transplant rejection) in the recipient host due to its incompliance in structure and/or conformation as compared with that of a native cornea, as well as residual agents such as chemicals and enzymes used for decellularization purpose.

Accordingly, there exist in the related art a need of an improved process for producing a cornea, in which the native structure and conformation of a native cornea are preserved while immunogenic matters (e.g., any residual cellular materials, chemicals and/or enzymes) are reduced to a level that the thus produced cornea may serve as a three-dimensional scaffold for host cells to grow thereon after transplantation without eliciting significant immune response and neovascularization.

SUMMARY

The present disclosure was created by the present inventors to overcome the above-noted problems in the production of an acellular cornea, and uses thereof.

Accordingly, it is the first aspect of this disclosure to provide a method for producing an acellular cornea. The method comprises subjecting a cornea of an animal to the treatment of a supercritical fluid (SCF); wherein, the method is characterized in not having the step of treating the cornea with any of a protease, a chelating agent, a detergent, a glycerol, or a combination thereof.

According to some embodiments, the method further includes the step of, prior to the treatment of SCF, immersing the cornea in water, or in a salt solution containing 0.5-4.0 M NaCl for at least 24 hours.

According to some embodiments, the cornea is treated with a supercritical fluid (SCF) in the presence of a co-solvent under a pressure of about 73-500 bar at a temperature between 30-50° C. for about 20-120 min.

The SCF may be any of a supercritical carbon dioxide ($ScCO_2$), a supercritical nitrous oxide ($ScN_2O$), a supercritical alkane, a supercritical alkene, a supercritical alcohol, a supercritical acetone or a combination thereof. In one example, the SCF is $ScCO_2$. In another example, the SCF is $ScN_2O$. The co-solvent may be a $C_{1-4}$ alcohol selected from the group consisting of, ethanol, propanol, isopropanol, butanol, isobutanol, sec-butanol, t-butanol, and cyclobutanol. Preferably, the co-solvent is 30-100% (v %) ethanol, more preferably, the co-solvent is 50-98% ethanol, and most preferably, 60-75% (v %) ethanol.

According to one preferred embodiment, the SCF treatment is carried out at a condition, in which the co-solvent is 60% (vol %) ethanol, the temperature is about 45° C., and the pressure is about 350 Bar, and the step is performed for about 80 min.

Most preferably, the present method does not include the step of treating the cornea with a protease, a chelating agent, a detergent, a glycerol solution, or a combination thereof.

According to some embodiments, the cornea may be obtained from an animal that is selected from the group consisting of, pig, cow, sheep, goat, rabbit, monkey, or human. Preferably, the cornea is obtained from pig.

It is therefore the second aspect of the present disclosure to provide an acellular cornea produced by the method described above.

According to preferred embodiments, the acellular cornea is derived from pig cornea.

Accordingly, the third aspect of the present disclosure is directed to a method of treating a subject suffering from an eye condition by use of the acellular cornea produced by the present disclosure. The method comprises steps of, implanting the acellular cornea of the present invention to the eye of the subject to repair the cornea damage associated with the eye condition.

In optional embodiments, the method further includes the step of, cultivating cells on the acellular cornea of the present invention before transplantation takes place. Suitable cells for cultivating on the acellular cornea of the present invention may be selected from the group consisting of, cornea endothelial cells, cornea stromal cells, cornea epithelial cells, embryonic stem cells, and adult stem cells.

According to some embodiments of the present disclosure, the cells are autologous.

According to other embodiments of the present disclosure, the cells are allogenic.

According to some embodiments of the present disclosure, the eye condition treatable by the present method is selected from the group consisting of, Fuchs' dystrophy, keratoconus, lattice cornea dystrophy, map-dot-fingerprint dystrophy, iridocorneal endothelial syndrome, iris nevus (Cogan-Reese) syndrome, Chandler's syndrome, and essential iris atrophy.

According to other embodiments of the present disclosure, the eye condition is the result of an infection caused by herpes simplex virus.

According to further embodiments of the present disclosure, the eye condition is the result of an infection caused by *Chlamydia trachomatis*.

According to still further embodiments of the present disclosure, the eye condition is the result of chemical burns.

The details of one or more embodiments of this disclosure are set forth in the accompanying description below. Other features and advantages of the invention will be apparent from the detail descriptions, and from claims.

It is to be understood that both the foregoing general description and the following detailed description are by examples, and are intended to provide further explanation of the invention as claimed.

BRIEF DESCRIPTION OF THE DRAWINGS

The accompanying drawings, which are incorporated in and constitute a part of the specification, illustrate various example systems, methods and other exemplified embodiments of various aspects of the invention. The present description will be better understood from the following detailed description read in light of the accompanying drawings, where.

DETAILED DESCRIPTION OF THE PREFERRED EMBODIMENTS

Figure 1:
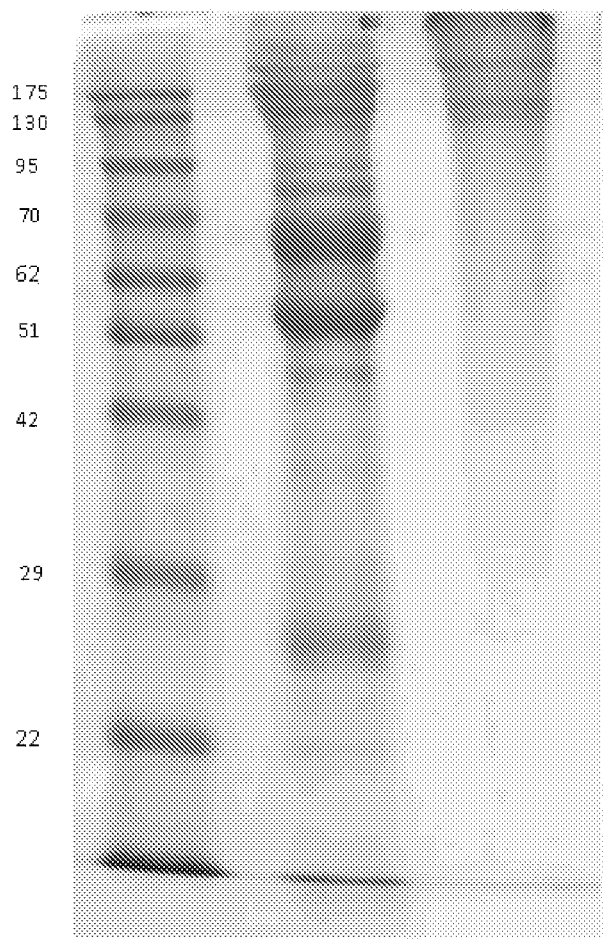
FIG. 1 illustrates the SDS PAGE analysis on soluble cornea total proteins extracted from (A) normal cornea tissue, and (B) $scCO_2$ treated cornea tissue in accordance with one embodiment of the present disclosure.

The detailed description provided below in connection with the appended drawings is intended as a description of the present disclosure and is not intended to represent the only forms in which the present disclosure may be constructed or utilized.

The singular forms "a", "and", and "the" are used herein to include plural referents unless the context clearly dictates otherwise.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The present disclosure pertains, among others, a novel method of producing an acellular cornea, the acellular cornea produced thereof, and uses of the thus produced acellular cornea for treating eye disorders and/or conditions that benefit therefrom.

The first aspect of the present disclosure involves a method of producing an acellular cornea, in which the native structure and conformation of the cornea is preserved, thus may provide an optimal micro-environment for host tissue cells to grow thereon after transplantation.

Accordingly, the present method includes at least, the step of, subjecting a cornea of an animal to the treatment of a supercritical fluid (SCF), wherein, the method is characterized in not having the step of treating the cornea with a protease, a chelating agent, a detergent, a glycerol solution, or a combination thereof.

Before starting the present method, the cornea along with some sclera tissue are removed from the eye ball of an animal. Animals suitable for use in the present disclosure include, but are not limited to, pigs, cattle, cows, sheep, goats, rabbits, monkeys, and human. In one preferred embodiment, the eyeball of a pig is held in a tissue holder ring, then the cornea along with some sclera tissue are cut from the eyeball with the aid of a trephine, and are immediately used in the present method.

The afore-obtained cornea is then subject to a decellularization process. The decellularization process is performed for the purpose of removing the cellular materials from the cornea, while preserving the physical and biochemical properties of the cornea tissue, so that it may better serve as a tissue scaffold. Accordingly, the cornea is subject to the treatment of a supercritical fluid (SCF) in the presence of a co-solvent under a pressure of about 73-500 bar at a temperature between 30-50° C. for about 20-120 min.

The SCF may be any of a supercritical carbon dioxide ($ScCO_2$), a supercritical nitrous oxide ($ScN_2O$), a supercritical alkane, a supercritical alkene, a supercritical alcohol or a supercritical acetone. In one example, the SCF is $ScCO_2$. In another preferred example, the SCF is $ScN_2O$. The co-solvent may be a $C_{1-4}$ alcohol, which includes but is not limited to, ethanol, propanol, isopropanol, butanol, isobutanol, sec-butanol, t-butanol, and cyclobutanol. In some preferred examples, the co-solvent is 30-100% (v %) ethanol, such as 30, 35, 40, 45, 50, 55, 60, 65, 70, 75, 80, 85, 90, 95, 96, 97, 98, 99 and 100% (vol %) ethanol. More preferably, the co-solvent is 40-98% ethanol, such as 40, 45, 50, 55, 60, 65, 70, 75, 80, 85, 90, 95, 96, 97, and 98% (vol %) ethanol. Even more preferably, the co-solvent is 60-75% (v %) ethanol, such as 60, 65, 70, and 75% (v %) ethanol. Most preferably, the co-solvent is 60% (v %) ethanol.

The decellularization process is performed at a condition, in which the pressure is about 70-500 bar, such as 70, 71, 72, 73, 74, 75, 76, 77, 78, 79, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, and 500 bar; preferably about 73-450 bar, such as 73, 74, 75, 76, 77, 78, 79, 80, 90, 100, 110, 120, 130, 140, 150, 160 170, 180, 190, 200, 210, 220, 230, 240, 250, 260, 270, 280, 290, 300, 310, 320, 330, 340, 350, 360, 370, 380, 390, 400, 410, 420, 430, 440, and 450 Bar; more preferably about 250-400 bar, such as 250, 260, 270, 280, 290, 300, 310, 320, 330, 340, 350, 360, 370, 380, 390, and 400 bar; the temperature is between 30-50° C., such as 30, 31, 32, 33, 34, 35, 36, 37, 38, 39, 40, 41, 42, 43, 44, 45, 46, 47, 48, 49 and 50° C., preferably about 35-48° C., such 35, 36, 37, 38, 39, 40, 41, 42, 43, 44, 45, 46, 47, and 48° C.; and for about 20-120 min, such as 20, 30, 40, 50, 60, 70, 80, 90, 100, 110 and 120 min, preferably about 30-90 min, such as 30, 40, 50, 60, 70, 80, and 90, min. In preferred embodiments, the solution treated cornea of step (1) is further treated with $ScCO_2$ in the presence of 60% (v %) ethanol at about 350 bar, 45° C., for about 80 min. The cornea would lose its transparency or become opaque after the decellularizaton process.

The preset method is characterized in not having the steps of subjecting the cornea to an enzymatic digestion (e.g., protease or nuclease treatment), and/or an ion chelation treatment (e.g., by use of an ion chelating agent), as described in the prior methods, see for example, CN Patent No. 104001215B, and U.S. Pat. No. 8,313,893B2. Nor is the cornea of the present invention subject to the treatment of a detergent. The enzymatic digestion herein refers to treating the cornea with a protease, which includes, but is not limited to, pepsin, trypsin, chymotrypsin, papain, chymopapain, bromelain, actinidain, proteinase A, proteinase K, peptidase, ficin, calpain, caspase, and a combination thereof; or a nuclease, which may be a DNA nuclease or a RNA nuclease. The ion chelation treatment herein refers to treating the cornea with a metal ion chelating agent, which includes, but is not limited to, ethylenediamine tetraacetic acid (EDTA), 1,4,7,10-tetraazacyclododecane-1,4,7,10-tetraacetic acid (DOTA), 1,4,7,10-tetraazacyclododecane-1,4,7,1-0-tetrakis (methylene phosphonic acid) (DOTP), trans-1,2-diaminocyclohexant-etra-acetic acid (CDTA), 4,5-dihydroxybenzene-1,3-disulphonic acid (Tiron), thiourea, 8-hydroxyquinoline-5-sulphonic acid, 3,6-disulpho-1,8-dihydroxy-naphthalene, Eriochromeschwarz T (1-(1-hydroxy-2-naphthylazo)-2-hydroxy-5-nitro-4-naphthalene sulphonic acid), and ammonium purpurate. The detergent treatment herein refers to treating the cornea with a detergent, particularly a liquid detergent consists of amphiphilic molecules, such as surfactants that are cationic (e.g., quaternary ammonium compounds), anionic (e.g., alkylbenzesulfonates, bile acids and the like) or non-ionic (e.g., Tween, Triton and/or Brij series). Further, the cornea of the present invention does not need to be immersed in a glycerol solution either, as required by some conventional processes.

According to optional embodiment, prior to the SCF treatment, the cornea is immersed in water or in a salt solution to remove the epithelium layer therefrom. According to some embodiments of the present disclosure, the solution contains monovalent salts, which include but are not limited to, lithium chloride, sodium chloride, potassium chloride, ammonium chloride and etc.

Preferably, the salt solution is a sodium chloride solution with a concentration of about 0.5 to 4 M, such as 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9 and 4.0 M; more preferably, about 1.0 to 3.5 M, such as 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, and 3.5 M; and most preferably, about 1.5 M. Preferably, the cornea is soaked in 1.5 M NaCl solution, in which no additional metal chelating agent (e.g., ethylenediamine tetraacetic acid (EDTA) is added, at room temperature with gentle shaking, for about 24 hrs. In other embodiments, the cornea is soaked in purified water for at least 24 hrs, prior to the SCF treatment. After treating with the salt solution or the purified water, the cornea appears to be opaque or non-transparent, and swollen. The condition of this optional water or salt solution treatment (e.g., treatment time, and/or the concentration of the salt therein) may be easily adjusted by a skilled artisan in this field based on the condition of each cornea that underwent the treatment, without undue experimentation. In other examples, the cornea is treated with a KCl solution (0.5 to 4 M) for at least 24 hours.

It is therefore a further aspect of the present disclosure to provide an acellular cornea produced by the method described above. The thus produced acellular cornea retains the integrity of collagen fibers of a native cornea, and is devoid of any cellular matters that may be immunogenic to a host, thus may serve as an excellent graft for host cells, particularly cornea derived cells, to grow thereon after transplantation, without inducing undesired post-graft responses to its host.

Accordingly, a further aspect of the present disclosure is directed to a method of treating a subject suffering from an eye disease, in which the subject may benefit from the graft of the acellular cornea that allows cells, (e.g., cornea derived cells) to grow thereon and repair any cornea damage resulted from a disease, an infection, or an accident (e.g., chemical burns).

The method in this respect comprises implanting the acellular cornea to the eye of the subject to repair the cornea damage associated with the eye condition.

The acellular cornea produced by the method described above is suitable for use as a biological scaffold for cells to grow thereon, accordingly, in optional embodiments, the acellular cornea of the present disclosure may be pre-cultivated with cells in vitro before being used in transplantation. The cells may be cultivated in accordance with any cell cultivating technique known in the art. Examples of cells that may be cultivated thereon include, but are not limited to, cornea derived cells such as cornea endothelial cells, cornea stromal cells, and cornea epithelial cells; embryonic stem cells, and adult stem cells. Further, the cells may be autologous (i.e., derived from the host receiving the acellular cornea as a graft) or allogenic (i.e., derived from a subject that is other than the host).

The present acellular cornea, after being cultivated with suitable cells, may then be transplanted into a host suffering from an eye condition associated with a cornea damage that requires a cornea transplant. The eye condition associated with a cornea damage may be resulted from a disease, an infection or an accident.

According to some embodiments, the eye condition is resulted from a disease selected from the group consisting of, Fuchs' dystrophy, keratoconus, lattice cornea dystrophy, map-dot-fingerprint dystrophy, iridocorneal endothelial syndrome, iris nevus (Cogan-Reese) syndrome, Chandler's syndrome, and essential iris atrophy. Fuchs' dystrophy occurs when endothelial cells are lost resulting in inefficient removal of liquid from the stroma that causes the cornea to swell and distort vision; ultimately the epithelial layer begins to swell resulting in abnormal curvature of the eyeball resulting in further distortion of vision. Keratoconus is a disorder resulting in the progressive thinning of the cornea, which gradually bulges outward resulting in an abnormal curvature. Another disease that may be treated by the present method is lattice dystrophy, which results in the accumulation of amyloid deposits or abnormal protein fibers in the stroma that leads to an increase in opaqueness resulting in reduced vision. In severe cases, this can result in erosion of the outer epithelial layer resulting in a condition known as epithelial erosion that requires a cornea transplant. Map-dot-fingerprint dystrophy is also known as Cogan's dystrophy, and is a degenerated disorder that affects the anterior cornea, causing characteristic slit lamp findings that leads to decreased vision and/or recurrent cornea erosions. Iridocorneal endothelial syndrome is common in women and results in changes in color of the iris, swelling of the cornea and the development of glaucoma. The syndrome is defined by a group of three linked conditions referred to as iris nevus syndrome; Chandler's syndrome or essential iris atrophy. However a common feature of this group of diseases is the migration of endothelial cells off the cornea and onto the iris. The loss of endothelial cells from the cornea results in cornea swelling and distortion of the iris with distortion of vision.

In other embodiments, the eye condition associated with cornea damage is caused by a number of pathogenic agents, such as a viral infection caused by herpes simplex virus; or a bacterial infection caused by *Chlamydia trachomatis*.

In further embodiments, the eye condition associated with cornea damage is resulted from accidents, such as chemical burns caused by acid based chemicals (e.g., muriatic acid, sulphuric acid found in batteries) and/or alkali based chemicals (e.g., lime, oven cleaners, ammonia). In severe cases the cornea becomes scarred to the extent that the only corrective measure is cornea transplantation.

According to one preferred embodiment of the present disclosure, the acellular cornea produced by the present method is directly applied to a wounded eye of an animal (i.e., a rabbit), in which the eye is injured to an extent that a cornea transplant is required. In this embodiment, the acellular cornea has not been seeded with epithelium cells. After implantation, the subject animal (i.e., the rabbit) is capable of making a full recovery (i.e., regain integrity of the wounded cornea) on its wounded eye.

The present invention will now be described more specifically with reference to the following embodiments, which are provided for the purpose of demonstration rather than limitation. While they are typically of those that might be used, other procedures, methodologies, or techniques known to those skilled in the art may alternatively be used.

EXAMPLES

Example 1

Preparation and Characterization of Acellular Porcine Cornea 1.1 Preparation of Acellular Porcine Cornea The frozen nucleated porcine eye stored at −20° C. was thawed at room temperature for less than 3 min before being clamped and held in place by a tissue holder. The cornea and a portion of sclera were removed from the eye by use of a trephine (18 mm). Immersed the removed cornea in a container (7 cm×5 cm×4 cm) containing 1.5M NaCl or water only (i.e., without the addition of any salt, chelating agent or protease). The entired container was then subject to gentle shaking at room temperature at a speed of 100 rpm for 24 hrs, which removed the epithelium layer (about 50 μm). At this stage, the NaCl or water treated cornea appeared to be swollen and opaque (i.e., non-transparent).

The NaCl or water treated cornea was then placed on a tissue holder, which was then inserted into a vessel of a $ScCO_2$ system (Helix SFE Version R3U, Applied Separations Inc (Allentown, Pa., USA)), in which 10 mL ethanol (75%) was present in the vessel. The $ScCO_2$ system was then operated at a pressure of 120 bar, at 38° C. for 60 min (i.e., a static and dynamic $ScCO_2$ treatment) to produce acellular cornea.

The acellular cornea was then stored at a sterilized condition until use.

1.2 Preparation of Acellular Porcine Cornea

In this example, the acellular porcine cornea was prepared in accordance with similar procedures as described in example 1.1, except the $ScCO_2$ system was operated at a pressure of 350 bar, at 45° C. for 80 min (i.e., a static and dynamic $ScCO_2$ treatment) to produce acellular cornea.

The thus obtained acellular cornea was stored at a sterilized condition until use.

1.3 Characterization of the Acellular Porcine Cornea of Example 1.2

The acellular cornea of examples 1.2 was analyzed by hematoxylin and eosin staining (H&E staining), 4',6-diamidino-2-phenylindole (DAPI) staining, as well as SDS-page analysis by following the standard protocols.

The quantified results from DAPI staining indicated that the normal cornea had a relatively high level of DNA counts, in which the amount of DNA was determined to be 37.29±5.3 (ng/mg), whereas the DNA level in the acellular cornea of example 1.2 was merely 11.51±0.74 (ng/mg), which suggested that the present $ScCO_2$ treatment was effective in removing cellular matters from the cornea tissue.

Figure 2A:
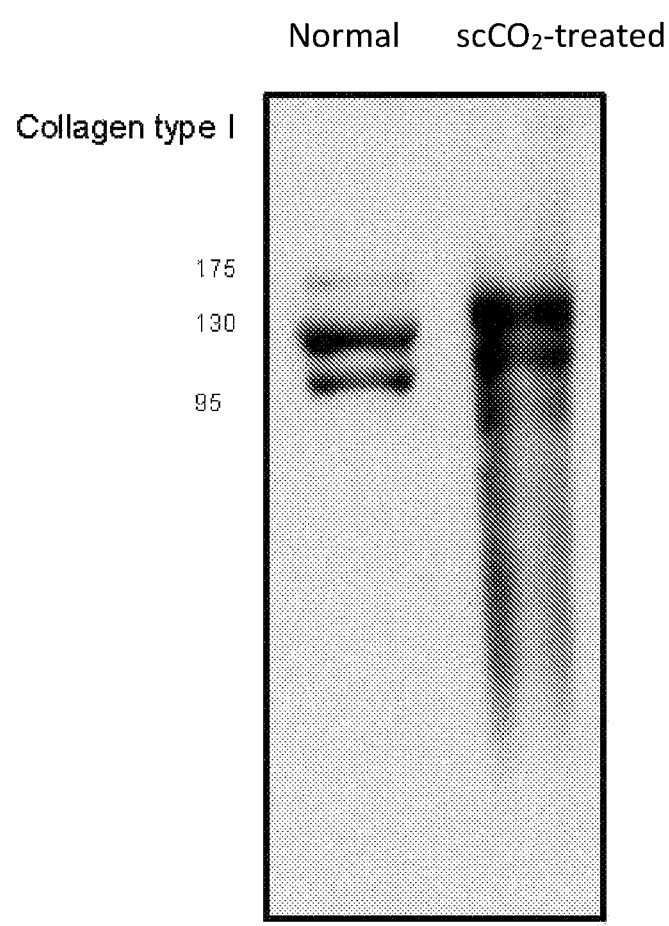
FIG. 2A is the western blot analysis on type I collagen of the normal cornea tissue and $scCO_2$ treated cornea tissue in accordance with one embodiment of the present disclosure.
Figure 2B:
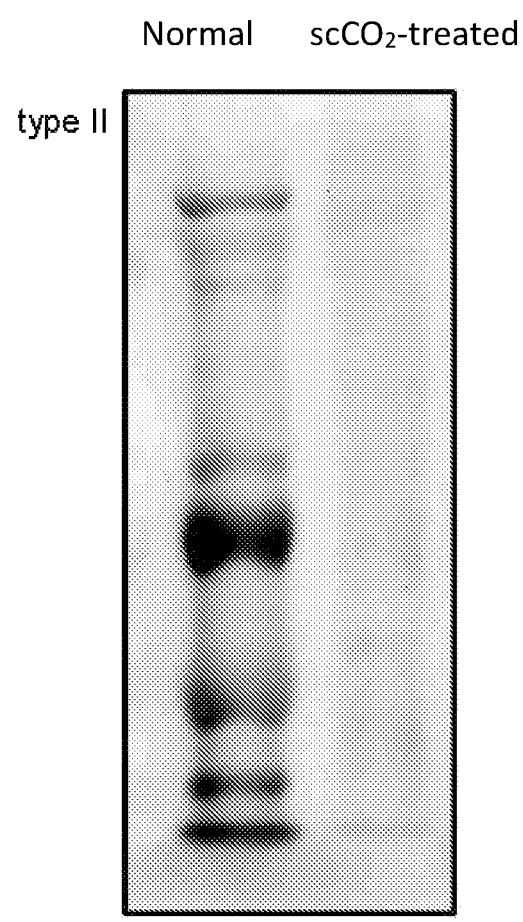
FIG. 2B is the western blot analysis on type II collagen of the normal cornea tissue and $scCO_2$ treated cornea tissue in accordance with one embodiment of the present disclosure.

SDS PAGE analysis also confirmed that, proteins remained in the cornea of example 1.2 after the $ScCO_2$ treatment were collagens (FIG. 1), particularly, type I collagen, as confirmed by western blot (FIG. 2B).

Figure 3:
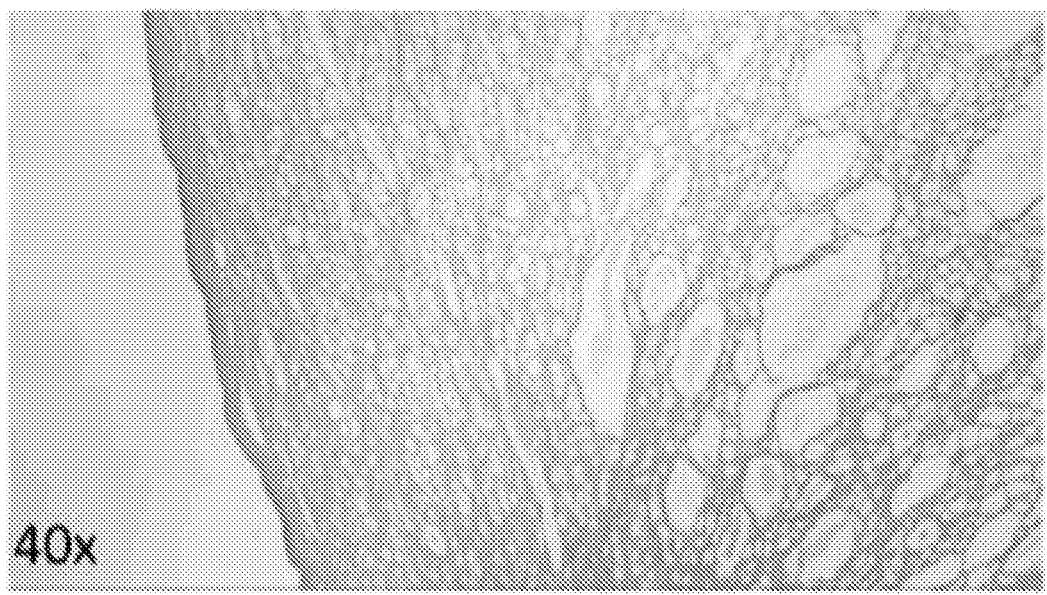
FIG. 3 are histological staining photographs of the acellular cornea of examples 1.2 respectively at the magnitude of 40× (A) and 100× (B)
Figure 3:
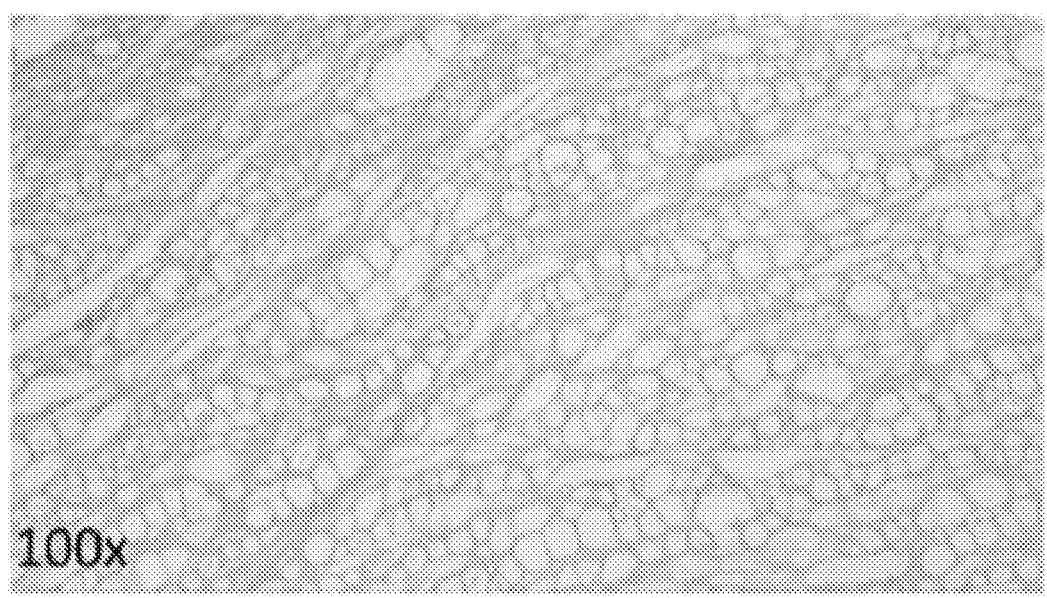

FIG. 3 are photographs from H&E staining of the cornea of example 1.2 at the magnification of 40× (panel A) and 100× (panel B), respectively. It was evident that the cornea of example 1.2 possessed relatively intact fibril structure, thus may serve as a biological scaffold for cells to grow thereon after transplantation.

Example 2

Re-growth of Human Adipose Cells (hADCs) on the Acellular Porcine Cornea of Example 1.2

2.1 Isolation of hADCs

Human adipose cells (hADCs) were isolated from fat tissues taken from patients underent liposuction surgery. Briefly, about 50 g fat tissue was rinsed with surplus amounts of phosphate-buffered saline (PBS) to remove any residual red blood cells. The thoroughly rinsed fat tissue was then suspended in PBS and subjected to centrifugation, and the upper layer was collected. Repeated the centrifugation once, and collected the upper layer, then evenly divided the collected upper layer into several portions. Each portion of the fat tissue was then transferred to another clear test tube containing 40 mL Dulbecco's Modified Eagle Medium (DMEM), which contained collagenase (1 mg/mL), N-acetyl-cysteine (NAC) (2 mM), and L-ascorbic acid 2-phosphate (0.2 mM). The test tubes were cultured at 37° C. overnight, then respectively subjected to centrifugation to remove the collagenase containing upper layer. The pellet in each tubes was harvested and cultured in DMEM supplemented with 10% fetal bovine serum (FBS), NAC (2 mM), and L-ascorbic acid 2-phosphate (0.2 mM) at 5% $CO_2$. The next day, the unattached cells were rinsed off by PBS, and additional 5 mL K-NAC was added therein. The culture medium was changed every two days until it reached confluence, which took about 1 week of time. The cells were harvested by trypsinization and stored in liquid nitrogen until further use.

2.2 The Acellular Porcine Cornea of Example 1.2 Supports the Growth of hADCS Thereon Before seeding, the acellular porcine cornea of example 1.2 was immersed in a 70% glycerol solution containing a mixture of antibiotics (penicillin, streptomycin, and amphotericin B) for 3 days, washed thoroughly with PBS, which also contained the mixture of antibiotics, then about $1 \times 10^4$ of the hADCs of example 2.1 were seeded thereon, and the cornea was then cultured for 14 days. Small samples of the cornea were taken at days 1, 3, 7 and 14, respectively, and subjected to H&E staining and SEM analysis. One representative results are depicted in FIG. 4.

Figure 4:
FIG. 4 are SEM photographs of the acellular cornea of examples 1.2 respectively at magnitude of 2,000× (A) before and (B) after seeding hADCs in accordance with one embodiment of the present disclosure.
Figure 4:
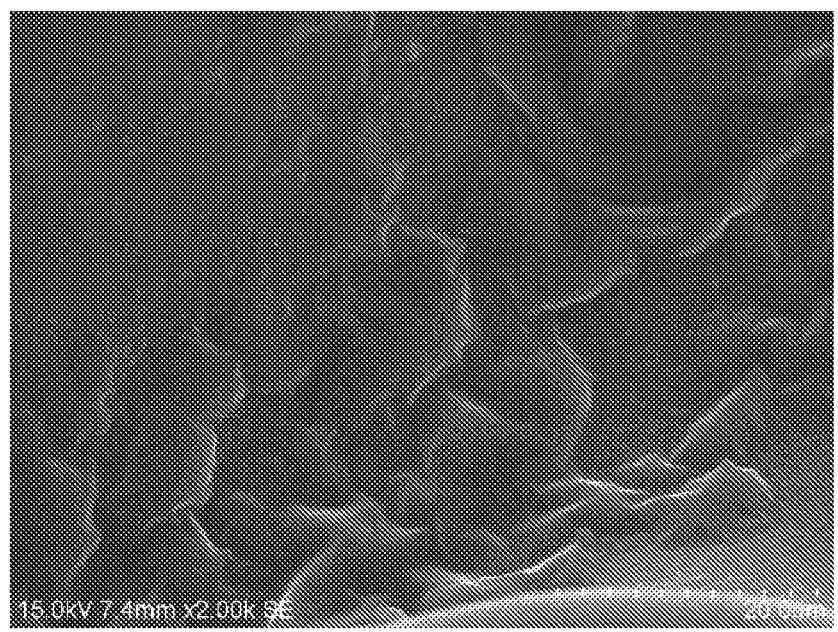

The SEM photographs in FIG. 4 are respectively taken from the acellular cornea of example 1.2 before (FIG. 4A) and after hADCs were seeded thereon for 7 days (FIG. 4B). It is evident that the acellular porcine cornea of example 1.2 may act as a scaffold to support the growth of hADCS thereon.

Example 3

Use of Acellular Porcine Cornea of Example 1.2 in a Corneal Xenograft Transplantation Model The effect of acellular porcine cornea of example 1,2 in repairing eye conditions that required a transplantation was evaluated in a corneal xenograft transplantation model.

For this purpose, the animals used were New Zealand White rabbits (Livestock Research Institute, Council of Agriculture, Executive Yuan), and are maintained in rigid accordance to relevant guidelines on the use of animals in research. One eye is randomly assigned to receive the corneal graft. Rabbits weighing between 2.0 and 3.0 kg are anesthetized by intramuscular injection of 0.5-0.7 mL/kg rodent cocktail (100 mg/mL ketamine, 20 mg/mL xylazine, and 10 mg/mL acepromazine). Topical anesthetic drops of proparacaine hydrochloride (0.5% Ophthaine, Bristol-Myers Squibb) are instilled into the animal's eye together with drops of cyclopentolate (1%, Cyclogyl®, Alcon, Ft. Worth, Tex.) and phenylephrine (10.0% CibaVision, Duluth, Ga.) to achieve maximal dilation of the pupil. All operations are performed under an operating microscope. About 5 mm wound was created on the cornea by use of the DALK (deep anterior lamellar keratoplasty) procedures. Then, the wound was covered with the acellular cornea of example 1.2 (about 6 mm in diameter), which was sutured into the cornea using 10-0 nylon suture. Topical eye drop containing 1% prednisolone was applied onto the eye 3 times per day, and continued for 7-10 days. Three weeks after the surgery, the eyes were stained with fluorescein to evaluate the integrity of the cornea. Images of the eye were also taken respectively at days 1, 5, 11, 14 and 21. At the end of the experiment, animals were sacrificed and stained for epithelial cells newly grown on the implanted cornea of example 1.2.

It was surprisingly and unexpectedly found that the rabbit underwent DALK surgery and subsequently implanted with the acellular cornea of example 1.2 was capable of regaining the integrity of the cornea, and epithelial cells newly migrated from neighboring area (i.e., unwounded area) were found to grow thereon the implanted cornea graft.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of the present disclosure.

What is claimed is:

1. A method of producing an acellular cornea comprising subjecting a cornea of an animal to the treatment of a supercritical fluid (SCF), which is conducted in the presence of 60% ethanol under a pressure of 350 bar at a temperature of 45° C. for 80 min; wherein the method is characterized in not having the step of treating the cornea with any of a protease, a chelating agent, a detergent, a glycerol, or a combination thereof; and prior to the SCF treatment, the cornea is subjected to the treatment of a salt solution containing 0.5-4.0 M NaCl for at least 24 hours.

2. The method of claim 1, wherein the SCF is any of a supercritical carbon dioxide ($ScCO_2$), a supercritical nitrous oxide ($ScN_2O$), a supercritical alkane, a supercritical alkene, a supercritical alcohol, a supercritical acetone or a combination thereof.

3. The method of claim 2, wherein the SCF is $ScCO_2$.

4. The method of claim 2, wherein the SCF is $ScN_2O$.

5. The method of claim 1, wherein the animal is selected from the group consisting of, pig, cow, sheep, goat, rabbit, monkey, or human.

6. The method of claim 5, wherein the animal is a pig.

* * * * *